(12) United States Patent
Losikoff et al.

(10) Patent No.: US 10,188,710 B2
(45) Date of Patent: Jan. 29, 2019

(54) REGULATORY T CELL EPITOPE AND HEPATITIS C VIRUS HOMOLOG

(71) Applicants: Rhode Island Council on Postsecondary Education, Warwick, RI (US); EpiVax, Inc., Providence, RI (US); Phyllis Losikoff, Sharon, MA (US); Stephen A. Gregory, Providence, RI (US)

(72) Inventors: Phyllis Losikoff, Sharon, MA (US); Stephen Gregory, Providence, RI (US); Anne DeGroot, Providence, RI (US); William Martin, Cumberland, RI (US)

(73) Assignee: Rhode Island Council on Postsecondary Education, Warwick, RI (US)

( * ) Notice: Subject to any disclaimer, the term of this patent is extended or adjusted under 35 U.S.C. 154(b) by 0 days.

(21) Appl. No.: 14/547,981

(22) Filed: Nov. 19, 2014

(65) Prior Publication Data
US 2015/0273032 A1    Oct. 1, 2015

Related U.S. Application Data

(60) Provisional application No. 61/899,617, filed on Nov. 4, 2013.

(51) Int. Cl.

| | |
|---|---|
| C07H 21/04 | (2006.01) |
| A61K 35/12 | (2015.01) |
| A61K 35/17 | (2015.01) |
| A61K 38/04 | (2006.01) |
| A61K 39/00 | (2006.01) |
| C07K 14/005 | (2006.01) |
| A61K 38/00 | (2006.01) |

(52) U.S. Cl.
CPC ...... *A61K 39/0005* (2013.01); *A61K 39/0008* (2013.01); *C07K 14/005* (2013.01); *A61K 38/00* (2013.01); *A61K 2039/5256* (2013.01); *A61K 2039/57* (2013.01); *A61K 2039/577* (2013.01); *C12N 2770/24222* (2013.01); *C12N 2770/24234* (2013.01)

(58) Field of Classification Search
CPC .... A61K 38/00; A61K 31/7115; A61K 38/17; A61K 48/0066; C07K 14/705
See application file for complete search history.

(56) References Cited

FOREIGN PATENT DOCUMENTS

| WO | WO9821338 | * | 5/1998 |
|---|---|---|---|
| WO | WO2004/108753 | * | 12/2004 |

OTHER PUBLICATIONS

Castelain et al., "Hepatitis c virus p7 membrane protein quasispecies variability in chronically infected patients treated with interferon and ribavirin, with or without amantadine", 2007, Journal of Medical virology, 79:144-154.*

Losikoff, Phyllis T., et al. "HCV epitope, homologous to multiple human protein sequences, induces a regulatory T cell response in infected pafients." Journal of Hepatology, vol. 62, Issue 1 (2015), pp. 48-55.

* cited by examiner

*Primary Examiner* — Barry A Chestnut
(74) *Attorney, Agent, or Firm* — Milstein Zhang & Wu LLC; Duan Wu, Esq.

(57) ABSTRACT

A pharmaceutical composition used to suppress immunity in an animal, wherein the pharmaceutical composition comprises an isolated T-cell epitope peptide containing an amino acid sequence of PLLLLLLXLPXRA (SEQ ID NO: 5), wherein X is an amino acid.

13 Claims, 8 Drawing Sheets
Specification includes a Sequence Listing.

Medium alone

HCV_G1_p7_794

HCV_G1_NS4b_1941

SEQUENCE LISTING

```
<160> NUMBER OF SEQ ID NOS: 6

<210> SEQ ID NO 1
<211> LENGTH: 17
<212> TYPE: PRT
<213> ORGANISM: Hepatitis C virus

<400> SEQUENCE: 1

Trp Pro Leu Leu Leu Leu Leu Leu Ala Leu Pro Gln Arg Ala Tyr Ala
1               5                   10                  15

Gln

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide

<400> SEQUENCE: 2

Pro Leu Leu Leu Leu Leu Leu Ser Leu Pro Pro Arg Ala
```

```
<210> SEQ ID NO 3
<211> LENGTH: 24
<212> TYPE: PRT
<213> ORGANISM: Hepatitis C virus

<400> SEQUENCE: 3

Ala Ala Arg Val Thr Gln Ile Leu Ser Ser Leu Thr Ile Thr Gln Leu
1               5                   10                  15

Leu Lys Arg Leu His Gln Trp Ile
            20

<210> SEQ ID NO 4
<211> LENGTH: 18
<212> TYPE: PRT
<213> ORGANISM: Hepatitis C virus

<400> SEQUENCE: 4

Ile Ser Gly Ile Gln Tyr Leu Ala Gly Leu Ser Thr Leu Pro Gly Asn
1               5                   10                  15

Pro Ala

<210> SEQ ID NO 5
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 5

Pro Leu Leu Leu Leu Leu Leu Xaa Leu Pro Xaa Arg Ala
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic peptide

<400> SEQUENCE: 6

Pro Leu Leu Leu Leu Leu Leu Ala Leu Pro Gln Arg Ala
1               5                   10
```

REGULATORY T CELL EPITOPE AND HEPATITIS C VIRUS HOMOLOG

CROSS REFERENCE TO RELATED APPLICATION

This application claims priority from U.S. Provisional Application Ser. No. 61/899,617 filed Nov. 4, 2013, the entire content and substance of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Feb. 6, 2015, is named 9842_SL.txt and is 1,959 bytes in size.

GOVERNMENT SUPPORT

This invention was made with government support under Grant No. AI082642 awarded by National Institutes of Health. The government has certain rights in the invention.

BACKGROUND

Artificial induction of tolerance to self or to foreign antigens is the goal of therapy for autoimmunity, transplantation allergy and other diseases, and is also desirable in the context of therapy with autologous proteins and non-autologous proteins. Until recently, therapeutic tolerance induction relied on broad-based approaches that resulted in cellular depletion and cytokine profile alteration. These broad-based approaches weaken the immune system in general and leave many subjects vulnerable to opportunistic infections, autoimmune attack and cancer. There is a need in the art for less aggressive and more targeted approaches to the induction of immune tolerance.

Immune tolerance is regulated by a complex interplay between T cells, B cells, cytokines and surface receptors. Initial self/non-self discrimination occurs in the thymus during neonatal development where medullary epithelial cells express specific self protein epitopes to immature T cells. T cells recognizing self antigens with high affinity are deleted, but autoreactive T cells with moderate affinity sometimes avoid deletion and can be converted to so called 'natural' regulatory T cells ($T_{reg}$) cells. These natural $T_{reg}$ cells are exported to the periphery and provide for constant suppression of autoimmunity.

A second form of tolerance occurs in the periphery where mature T cells are converted to an 'adaptive' $T_{reg}$ phenotype upon activation via their T cell receptor in the presence of IL-10 and TGF-.beta. The possible roles for these 'adaptive' $T_{reg}$ cells include dampening immune response following the successful clearance of an invading pathogen as a means of controlling excessive inflammation as might be caused by an allergic reaction or low level chronic infection, or possibly to facilitate co-existence with beneficial symbiotic bacteria and viruses. 'Adaptive' $T_{reg}$ may also play a role in managing the life cycle of human antibodies that have undergone somatic hypermutation.

Natural regulatory T cells are a critical component of immune regulation in the periphery. Upon activation through their TCR natural Tregs are capable of suppressing bystander effector T cell responses to unrelated antigens through contact dependent and independent mechanisms. In addition the cytokines released by these cells including IL-10 and TGF-.beta., are capable of inducing antigen-specific adaptive Tregs. Despite extensive efforts, with few exceptions, the antigen specificity of natural Tregs, and more importantly natural $T_{reg}$ circulating in clinically significant volumes, is still unknown.

There is need in the art for the identification of new regulatory T cell epitopes contained in common autologous proteins such as IgG ("Tregitopes") and for methods for related to their preparation and of use.

Chronic hepatitis C virus (HCV) infection is a major public health concern worldwide. It is the leading cause of liver failure and reason for liver transplant in the US. Irrespective of clinical outcome, acute HCV infections are characterized by broad HCV-specific T cell responses that correlate with spontaneous viral clearance in a minority of individuals. In most patients, however, this initial response fails to contain the virus and chronic disease results. Increased numbers of $CD4^+$ regulatory $T_{(reg)}$ cells circulating in the bloodstream and accumulating in the liver have been implicated in the pathogenesis of chronic hepatitis C.

$T_{reg}$ cells constitute one of the major mechanisms underlying immunological homeostasis and self-tolerance. In addition, $T_{reg}$ cells play a key role in moderating the immune response to infectious diseases, suppressing host tissue and organ damage that would occur in the absence of regulation. Although key to maintaining immune homeostasis, a growing body of evidence suggests that $T_{reg}$ cells also contribute to the establishment and persistence of chronic infections, e.g., HCV. While no single marker exists, human $T_{reg}$ cells are classically identified by expression of the transcription factor, forkhead box P3 (FoxP3), and the cell surface expression of the interleukin (IL)-2 receptor a chain (CD25). Bystander suppression is an additional key feature of $T_{reg}$ cells.

Two distinct $T_{reg}$ cell subsets are described in the literature: natural (n)$T_{reg}$ cells specific for self epitopes and generated by high-avidity selection in the thymus, and inducible (i)$T_{reg}$ cells that derive from conventional ($CD4^+$ $CD25^-FoxP3^-$) T cells following stimulation in the periphery. n$T_{reg}$ cells can induce the conversion of conventional T cells to i$T_{reg}$ cells via cytokine-dependent and -independent mechanisms, a process called infectious tolerance. Notably, the factors that affect expansion of the $T_{reg}$ cell population in cases of chronic hepatitis C remain to be fully delineated. Nonetheless, the consensus supports the heterogeneous nature of the expanded $T_{reg}$ cell population composed of both n$T_{reg}$ and i$T_{reg}$ cell subsets.

BRIEF DESCRIPTION OF DRAWINGS

FIG. 1A: the production of CD3+CD4+FoxP3+ cells in cultures of PBMCs derived from HCV-infected patients for the medium alone.

FIG. 1B: HCV GI_p7_794 induces the production of CD3+CD4+FoxP3+ cells in cultures of PBMCs derived from HCV-infected patients.

FIG. 1C: the production of CD3+CD4+FoxP3+ cells in cultures of PBMCs derived from HCV-infected patients for HCV G1_NS4b_1941.

FIG. 1D: the production of CD4 cells shown in FIG. 1C, further showing amounts of C25 and C349.

FIG. 2: HCV_G1_p7_794 fails to elicit a significant increase m CD3+CD4+FoxP3+ cells in PBMC cultures derived from non-infected individuals or patients who spontaneously cleared infection.

Figure 3:
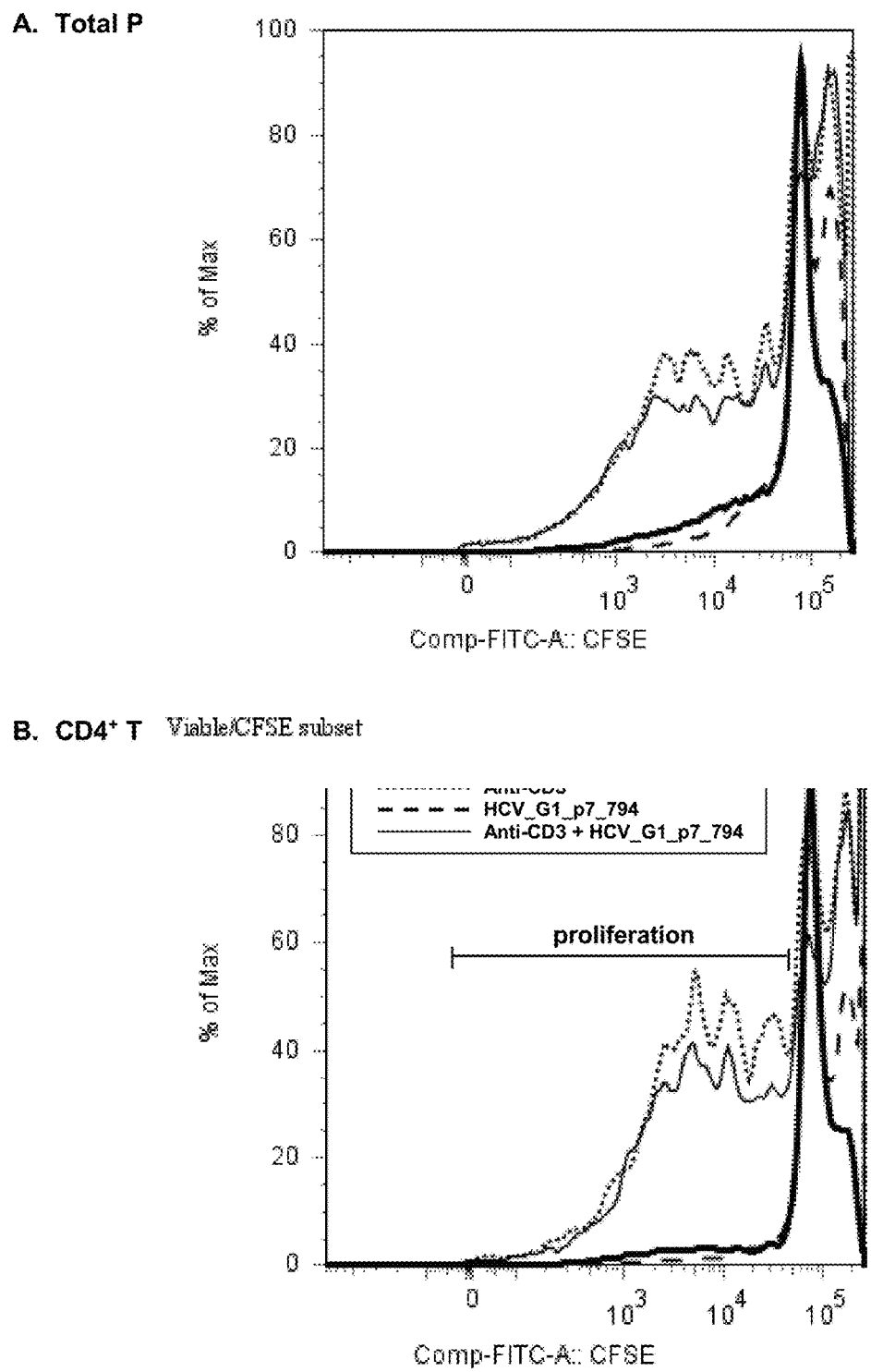

FIG. 3: CD3+CD4+FoxP3+ T cells do not proliferate in response to HCV_G1_p7_794.

Figure 4:
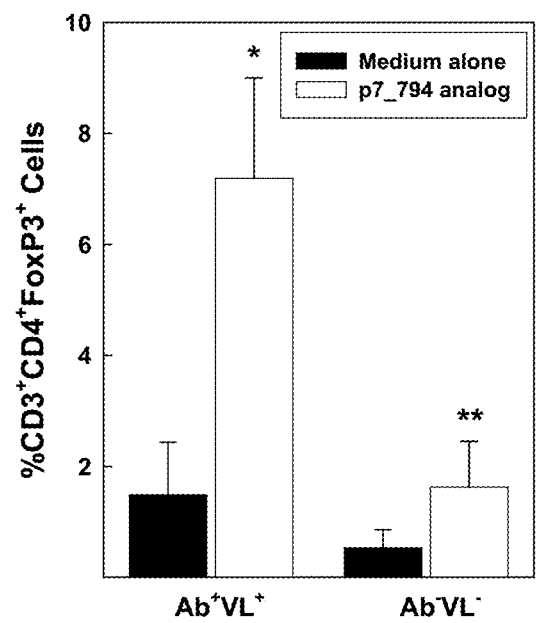

FIG. 4: Human p7_794 analog stimulates a significant increase in CD3+CD4+FoxP3+ T cells in HCV-infected and non-infected individuals.

Figure 5:
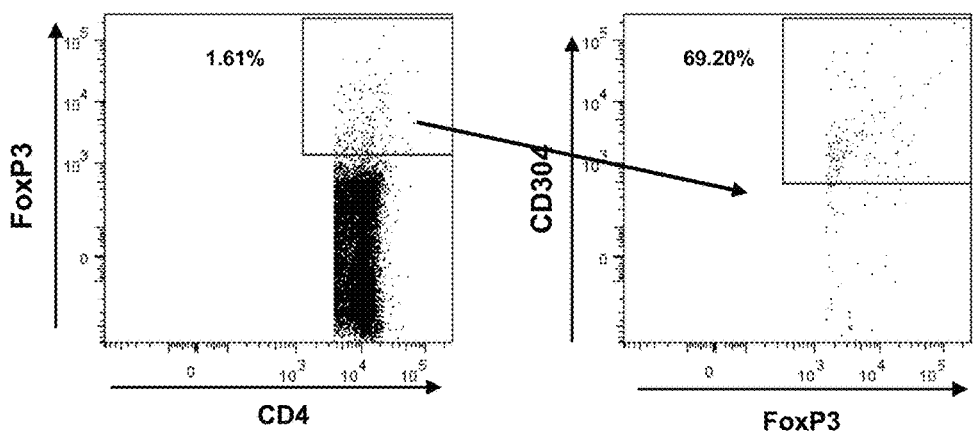
Figure 5:
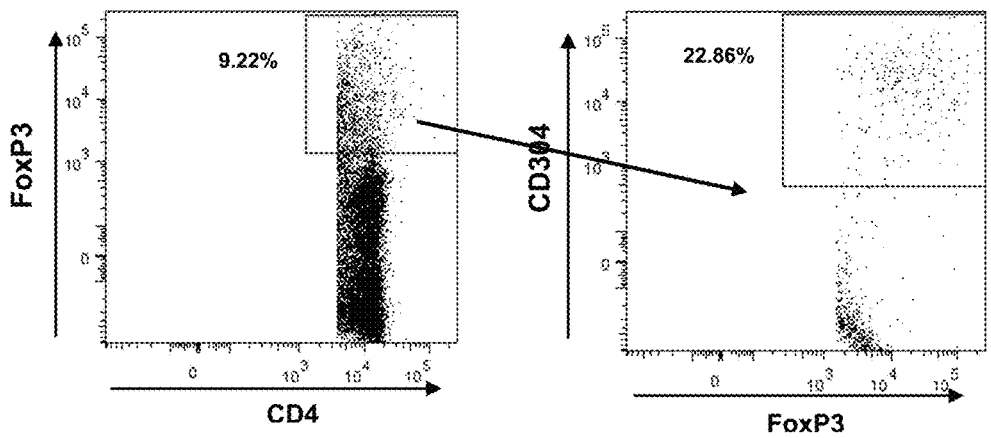

FIG. 5: Fewer HCV-G1_p7_794-responsive Treg cells express CD304 (neuropilin).

SUMMARY OF THE INVENTION

The present invention harnesses the functions of regulatory T cells ($T_{reg}$), particularly those cells that already regulate immune responses to foreign and self proteins in the periphery (pre-existing or natural $T_{reg}$). In one aspect, the invention provides T-cell epitope polypeptide compositions.

The selective engagement and activation of pre-existing natural Treg through the use of Tregitopes and Tregitope-antigen fusions, is therapeutically valuable as a means of treatment for any disease or condition marked by the presence of an unwanted immune response created by autoimmune diseases, such as, but not limited to, Crohn's Disease, Guillian Barre Syndrome, Lupus, Psoriasis, Rheumatoid Arthritis, Ulcerative Colitis and Multiple Sclerosis; pre- or post-transplanations; allergies such as, but not limited to, asthma, COPD and allergic rhinitis. The present invention is directed to the use of a peptide in the HCV p7 protein, HCV_G1_p7_794 (SEQ ID NO: 1), residing in the hepatitis C virus (HCV), for the control of unwanted immune response. A further embodiment is the human analog (SEQ ID NO: 2) of the HCV_G1_p7_794, H p7_794.

In one embodiment, the present invention is directed to a T-cell epitope polypeptide composition comprising at least one polypeptide selected from the group consisting of: SEQ ID NOS: 1 and 2. In a particular embodiment, the invention is directed to a pharmaceutical composition comprising a polypeptide of the invention and a pharmaceutically acceptable carrier.

In a second embodiment, the present invention is directed to a nucleic acid encoding at least one T-cell epitope polypeptide selected from the group consisting of: SEQ ID NOS: 1 and 2. In a particular embodiment, the invention is directed to a vector comprising a nucleic acid of the invention. In yet another embodiment, the invention is directed to a cell comprising a vector of the invention.

In a third embodiment, the invention is directed to a method of treating or preventing a medical condition in a subject in need thereof comprising administering a therapeutically effective amount of a T-cell epitope polypeptide selected from the group consisting of: SEQ ID NOS: 1 and 2. In a particular embodiment, the medical condition is selected from the group consisting of: an allergy, an autoimmune disease, a transplant related disorder, graft versus host disease, an enzyme or protein deficiency disorder, a hemostatic disorder, cancer, infertility; and a viral, bacterial or parasitic infection.

In fourth embodiment, the present invention is directed to a method for repressing immune response in a subject, comprising administering a composition comprising a therapeutically effective amount of a peptide comprising SEQ ID NOS: 1 or 2 to the subject, wherein the peptide represses the immune response. In a particular embodiment, the peptide suppresses effector T cell response. In a particular embodiment, the peptide suppresses helper T cell response. In another embodiment, the peptide suppresses B cell response.

In a fifth embodiment, the present invention is directed to a method of suppressing antigen specific immune response in a subject through the administration of a therapeutically effective amount of a composition comprising SEQ ID NOS: 1 or 2, wherein the one or more Tregitopes are either covalently bound, non-covalently bound or in admixture with a specific target antigen resulting in the diminution of immune response against the target antigen. In a particular embodiment, the suppressive effect is mediated by natural Treg. In another embodiment, the suppressive effect is mediated by viral homolog of the natural Treg. In another embodiment, the peptide suppresses effector T cell response. In another embodiment, the peptide suppresses helper T cell response. In another embodiment, the peptide suppresses B cell response.

In a sixth embodiment, the present invention is directed to a method for enhancing the immunogenicity of a vaccine delivery vector, comprising identification and removal of regulatory T cell epitopes residing in the vaccine to hepatitis C virus. In a particular embodiment, the T cell epitopes are selected from the group consisting of: SEQ ID NOS: 1 or 2. In a further embodiment, a vaccine delivery vector with removed regulatory T cell epitopes is further enhanced, comprising (a) isolating regulatory T-cells from the biological sample; (b) contacting the isolated regulatory T-cells with an effective amount of a Tregitope composition of the enhanced vaccine delivery vector; (c) identification of the sequences; and (d) removal of remaining regulatory T cell epitopes residing in the vaccine.

In a seventh embodiment, the present invention is directed to a method to reduce the repressing immune response in a subject infected with the hepatitis C virus, comprising administering a therapeutically effective of the antibody recognizing a peptide from the group consisting of: SEQ ID NOS: 1 and 2.

DETAILED DESCRIPTION OF INVENTION

Spontaneous resolution of hepatitis C virus (HCV) infections depends upon a broad T cell response to multiple viral epitopes. Most patients fail to clear infections spontaneously, however, and develop chronic disease. The elevated number and function of $CD3^+CD4^+CD25^+FoxP3^+$ regulatory $T_{(reg)}$ cells in HCV-infected patients suggest the role of $T_{reg}$ cells in impaired viral clearance. Factors contributing to increased $T_{reg}$ cell activity in chronic hepatitis C cases remain to be delineated.

Resolution of primary HCV infections is dependent upon the vigorous response of $CD4^+$ and $CD8^+$ T cells to multiple viral epitopes. HCV persists in the majority of infected patients, however, by modifying and/or evading the host immune response. Purportedly, a variety of factors contribute to the diminished T cell responses observed in chronically infected patients including: viral mutation and escape linked to both CD4 and CD8 T cell failure, CD4 T cell anergy, CD8 T cell exhaustion, impaired dendritic cell function, and $T_{reg}$ cell-mediated suppression. The increased frequency of $T_{reg}$ cells found in the liver and circulating in the peripheral blood of chronically-infected patients provided an initial indication of the role of $T_{reg}$ cells in the pathogenesis of chronic hepatitis C. It remained unclear until recently, however, whether this increase represented the HCV epitope-specific response of $T_{reg}$ cells or the nonspecific consequence of chronic inflammation and liver disease.

Immunoinformatics tools were used to predict promiscuous, highly-conserved HLA-DRB1-restricted immunogenic consensus sequences (ICS), each composed of 5-6 T cell epitopes. These sequences were synthesized and added to cultures of peripheral blood mononuclear cells (PBMCs)

derived from patients who resolved HCV infection spontaneously, patients with persistent infection, and non-infected individuals.

In the present invention, surprisingly a unique viral peptide derived from HCV p7 protein (HCV_G1_p7_794) was identified that promotes a $T_{reg}$ cell response among PBMCs derived from patients with persistent HCV infection. This peptide exhibited human homology when evaluated using GenBank Basic Local Alignment Search Tool (BLAST). Further analysis using a new bioinformatics tool, JanusMatrix, demonstrated that this HCV peptide cross-reacts with HLA matched peptide sequences located within hundreds of human proteins. Our invention showed that HCV_G1_p7_794 engages preexisting $nT_{reg}$ cells, as a consequence of this homology, induces infectious tolerance and the expansion an $iT_{reg}$ cell population, which contributes to suppression of effector $T_{(eff)}$ cell activity in cases of chronic HCV infection. Further, a virus-encoded peptide (HCV_G1_p7_794) with extensive human homology activates cross-reactive $CD3^+CD4^+CD25^+FoxP3^+$ $nT_{reg}$ cells, contributing to immunosuppression and chronic hepatitis C.

The invention provides methods of treating a subject with a medical condition comprising administering a therapeutically effective amount of a T cell epitope selected from the group consisting of: SEQ ID NOS: 1 or 2 in a pharmaceutically acceptable carrier or excipient. The T cell epitope of the present invention can be incorporated into pharmaceutical compositions suitable for administration. The pharmaceutical compositions generally comprise at least one T cell epitope and a pharmaceutically-acceptable carrier in a form suitable for administration to a subject. Pharmaceutically-acceptable carriers are determined in part by the particular composition being administered, as well as by the particular method used to administer the composition.

Example 1: a Peptide Sequence in HCV p7 Exhibits Human Homology

Sustained, virus-specific CD4 and CD8 T cell responses are associated with successful control of HCV infection. Therapeutic vaccination offers a rational approach to stimulating host resistance and overcoming viral persistent in cases of chronic disease. Toward this end, 20 promiscuous HCV (genotype 1) ICS were predicted and validated by demonstrating their ability to bind a panel of the eight common alleles HLA-DRB1 alleles: DRB1*0101, *0301, *0401, *0701, *0801, *1101, *1301, and *1501, representing essentially the entire human population. One ICS, located within HCV p7 protein (HCV_G1_p7_794; WPLLLLLLALPQRAYAQ (SEQ ID NO: 1)), exhibited significant human homology (>70% shared identities) determined by GenBank BLAST analysis; none of the remaining ICS exhibited the same homology.

HCV sequences were acquired from the Los Alamos sequence and immunology database. Nine-mer amino acid sequences, capable of fitting the binding groove of HLA class II molecules and highly conserved across HCV genotype 1a and 1b isolates, were identified using bioinformatics tools. Each 9-mer was scored for its predicted potential to bind a panel of eight HLA class II alleles (DRB1*0101, DRB1*0301, DRB1*0401, DRB1*0701, DRB1*0801, DRB1*1101, DRB1*1301 and DRB1*1501).

HLA class II immunogenic consensus sequences (ICS) were constructed by assembling potentially immunogenic 9-mers into 18-25 amino acid sequences. ICS construction improves the probability that an epitope will be presented in the context of more than one HLA allele, thus broadening the response of an HLA-diverse human population. Twenty ICS were synthesized as peptides using 9-fluoronylmethoxycarbonyl chemistry and purified >85% by 21st Century Biochemicals (Marlboro, Mass.). As predicted, each of these "promiscuous" ICS was bound by multiple HLA-DRB1 alleles in competitive binding assays performed in accordance with methods we described previously. Each ICS was also evaluated for human homology (>7 shared identities per 9-mer frame) using GenBank BLAST.

Example 2: HCV_G1_p7_794 Induces a $CD3^+$ $CD4^+FoxP3^+$ T Cell Response in HCV-Infected Patients HCV-seropositive subjects with persistent viremia ($Ab^+$ $VL^+$), patients who spontaneously resolved infection ($Ab^+$ $VL^-$) and HCV-seronegative, non-infected ($Ab^-VL^-$) individuals were recruited from the Rhode Island Adult Corrections Institution (ACI) to participate in this study. Recruitment methods and the population are described elsewhere. The Institutional Review Boards of the Miriam Hospital, Rhode Island Department of Corrections and Office of Human Research Protection approved this study. All HCV infected subjects included in these analyses were infected with HCV genotype 1a or 1b (Versant HCV genotype assay 2, Siemens Healthcare Diagnostics Inc.). Hartford Hospital Transplantation Research Laboratory (Hartford, Conn.) and the Cellular Mediated Immunology Core Laboratory at the University of Rhode Island (Providence, R.I.) performed HLA typing. Subject demographic and serologic data are shown in Table 1.

TABLE 1

| ID# | Age | HCV Status | Viral Load IU/ml | Geno-type | Anti-body | HLA-DRB1 |
|---|---|---|---|---|---|---|
| 229 | 28 | Infected | 170,620 | 1 | + | 03,11 |
| 236 | 29 | Infected | 602,611 | 1 | + | 01,11 |
| 261 | 25 | Infected | 7,464,611 | 1 | + | 01,11 |
| 265 | 22 | Infected | 21,917,190 | 1a | + | 13,15 |
| 272 | 23 | Infected | 458 | 1a | + | 03,11 |
| 279 | 25 | Infected | 1,788,326 | 1a | + | 13,15 |
| 282 | 28 | Infected | 186,678 | 1a | + | 03,04 |
| 216 | 23 | Clearer | NA | NA | + | 07:01 |
| 221 | 27 | Clearer | NA | NA | + | 03,11 |
| 222 | 25 | Clearer | NA | NA | + | 03,15 |
| 246 | 26 | Clearer | NA | NA | + | 01,04 |
| 267 | 23 | Clearer | NA | NA | + | 03,11 |
| 264 | 27 | Clearer | NA | NA | + | 03,11 |
| 248 | 26 | Non-infected | NA | NA | − | 04,11 |
| 259 | 26 | Non-infected | NA | NA | − | 04,11 |
| 262 | 22 | Non-infected | NA | NA | − | 03,11 |
| 257 | 22 | Non-infected | NA | NA | − | 03,15 |
| 263 | 26 | Non-infected | NA | NA | − | 01,03 |
| 268 | 21 | Non-infected | NA | NA | − | |

A series of experiments was undertaken to determine and compare the HCV_G1_p7_794-specific responses of PBMCs obtained from non-infected control individuals ($Ab^-VL^-$), patients who spontaneously cleared HCV infection ($Ab^+VL^-$) and infected patients in whom viremia persisted ($Ab^+VL^+$).

Cryopreserved PBMCs were thawed; suspended in HEPES-buffered RPMI1640 medium supplemented with 10% HuAB serum (Valley Biomedical, Winchester, Va.), glutamine, 100 U/ml penicillin and 100 μg/ml streptomycin; and rested overnight at 37° C. in a humidified, $CO_2$ incubator. On the following day, the PBMCs were centrifuged and resuspended in fresh medium containing 5% HuAB serum; $1\times10^6$ cells/nil were transferred to deep, flat-bottom, non-treated 48-well plates. The peptide sequence indicated in the text was added (10 µg/ml final concentration) and the cells were incubated for 5 days. PBMCs cultured in the presence of medium with 0.1% DMSO served as a negative control. Half the spent medium was replaced on day 3. The cells were collected for analysis on day 5.

For proliferation assays, cells rested overnight were labeled with carboxyfluorescein diacetate, succinimidyl ester (CFSE: Life Technologies Corporation, Carlsbad, Calif.) prior to culture in the presence or absence of 30 ng/ml anti-CD3 monoclonal antibody (clone HIT3a; BioLegend, San Diego, Calif.) and 10 µg/ml HCV_G1_p7_794. Cell proliferation was evaluated by flow cytometric analysis according to the protocol provided by Life Technologies in which a loss in fluorescence intensity correlates directly with the extent of replication.

The cells collected after 5 days incubation were quantified and characterized in accordance with methods we described previously. Dye-conjugated mouse monoclonal antibodies specific for the following determinants were purchased from BioLegend (San Diego, Calif.) and used: CD3, CD4 (clone OKT4), CD8a (clone HIT8a); CD39 (clone A1), and CD304 (clone 14H4); anti-human CD25 (clone M-A251) and anti-human FoxP3 (clone 236a) were purchased BD Biosciences (San Jose, Calif.). Data were collected on a 4 laser (13 color capability) BD LSRII Flow Cytometer (BD Biosciences, San Jose, Calif.) and analyzed using FlowJo software (Tree Star, Inc., Ashland, Oreg.). All analyses were conducted using the appropriate isotype controls to correct for non-specific staining PBMCs were cultured in the presence of medium alone, 10 µg/ml HCV_G1_p7_794, or 10 µg/ml HCV_G1_NS4b_1941.

The results were analyzed using the SigmaStat statistics program (Aspire Software International). Individual means were compared using a non-paired Student's t test or a Mann-Whitney Rank Sum test. Data derived from 3 or more groups were compared by one-way analysis of variance; the Dunnett's test was used to determine which groups differed significantly.

Figure 1A:
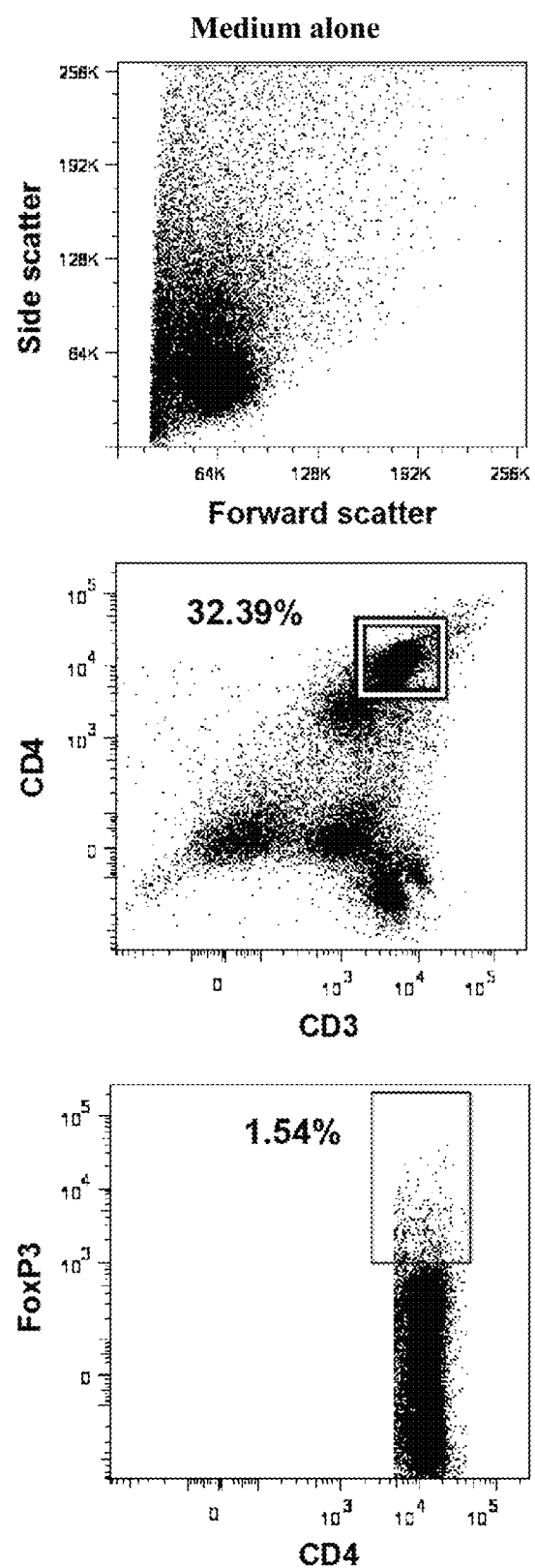
Figure 1B:
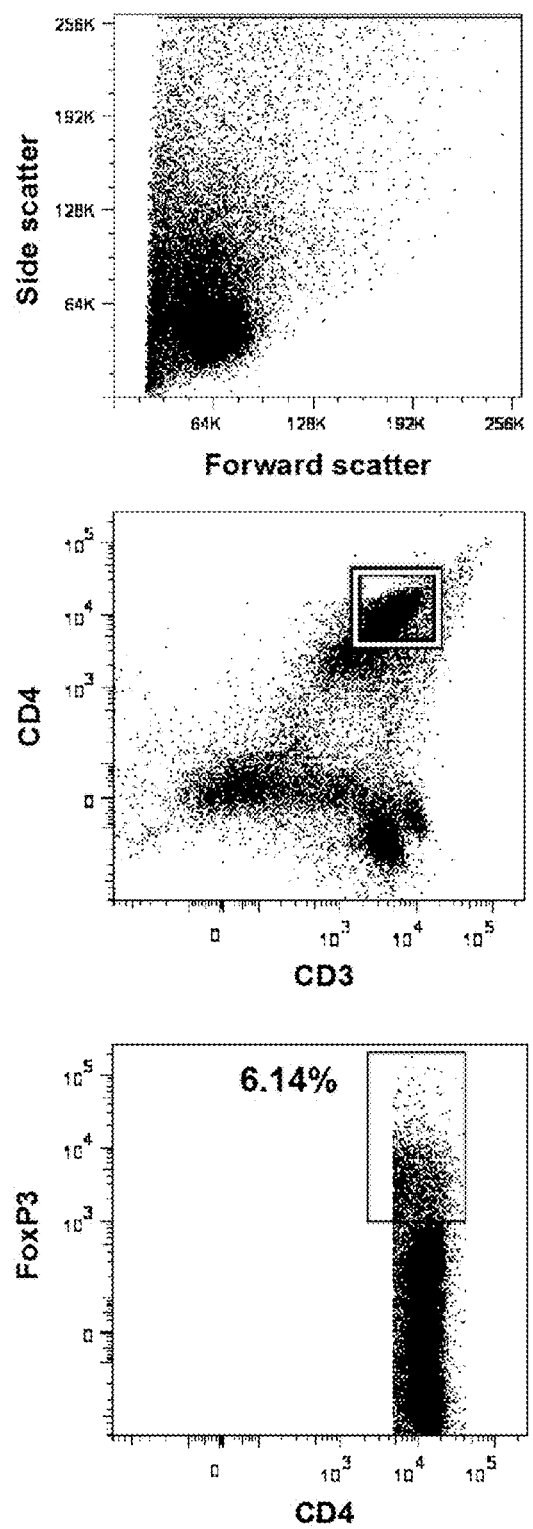
Figure 1C:
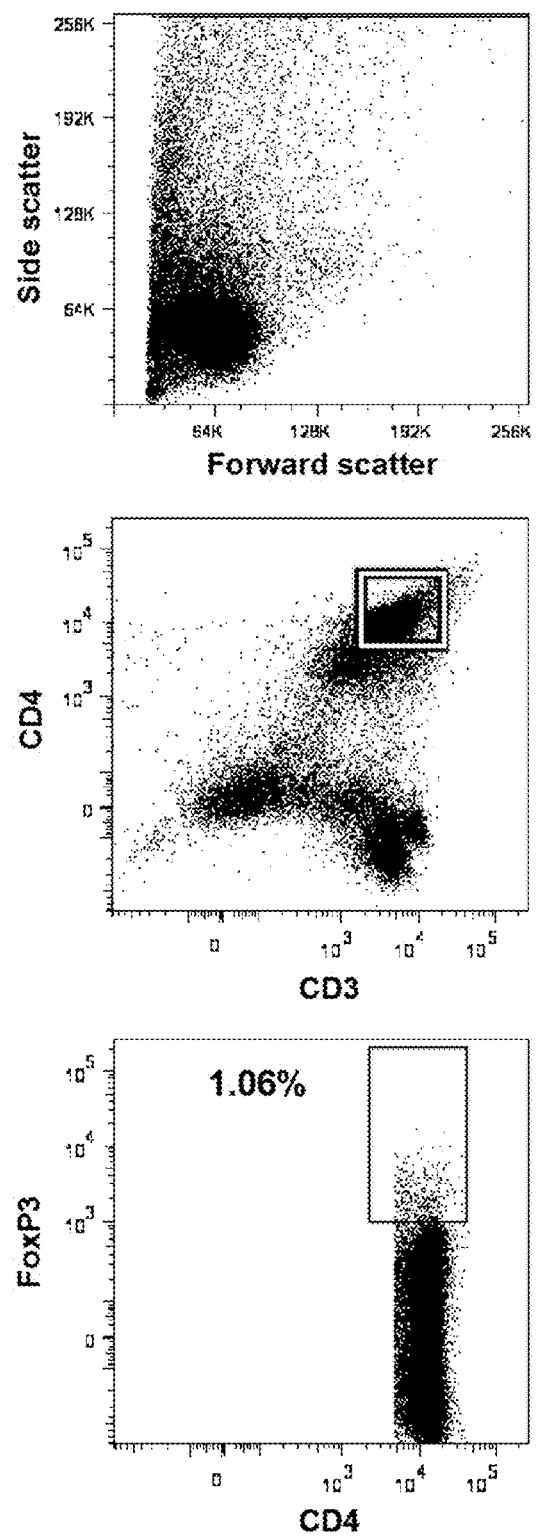

The cells were collected after 5 days incubation and analyzed by flow cytometry (FIGS. 1A-1C). The CD3+CD4+FoxP3+ cells were further characterized by the expression of CD25 and CD39 (FIG. 1B). The gating scheme and representative analyses are shown.

Figure 1D:
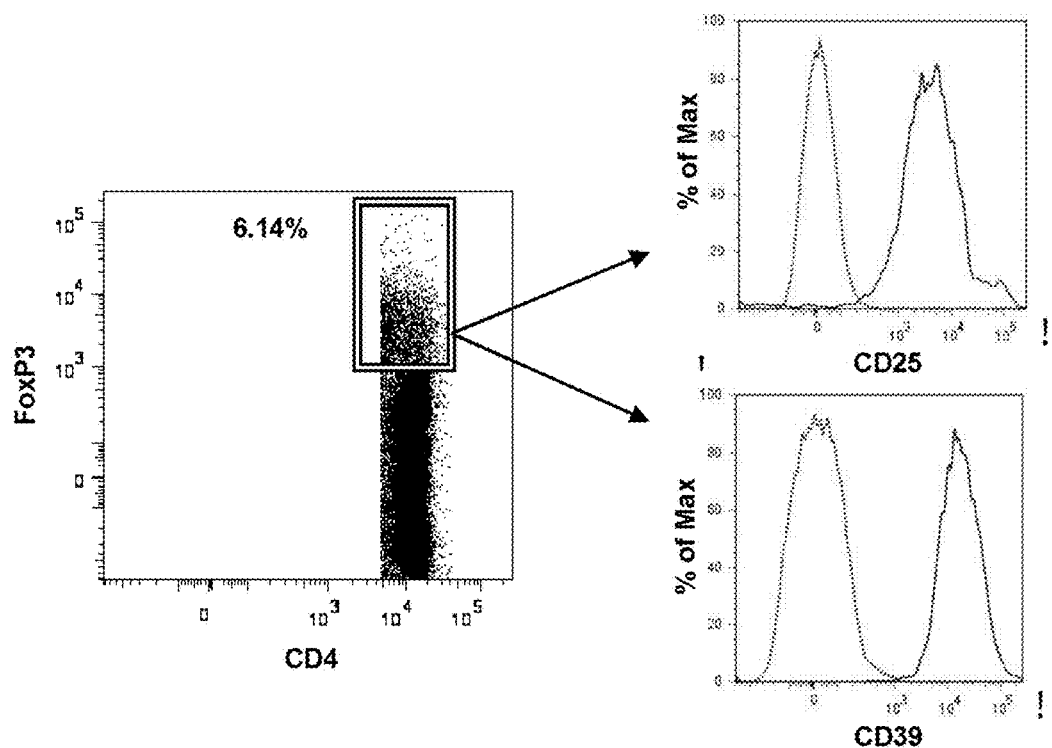

HCV_G1_p7_794 induced a marked increase in CD3+CD4+FoxP3+ cells when added to PBMC cultures derived from infected, Ab+vL+ patients (FIGS. 1A-1C). In contrast, HCV_NS4B_1941 (AARVTQILSSL TITQLLKRLHQWI; an ICS that exhibits little human homology) failed to promote an increase in CD3+CD4+FoxP3+ cells when added to PBMC cultures derived from Ab+vL+ individuals. Other highly conserved HCV ICS with negligible human homology (e.g., HCV_G1_NS4b_1769; ISGIQYLAGL-STLPGNPA) similarly failed to elicit a CD3+CD4+FoxP3+ cell response (data not shown). The CD3+CD4+FoxP3+ cells induced by the addition of HCV_G1_p7_794 to Ab+vL+ PBMC cultures expressed both CD25 (IL-2 receptor a chain, constituently expressed by Treg cells) and CD39, a cell ectonucleotidase associated with Treg cell suppressor function (FIG. 1D).

Figure 2:
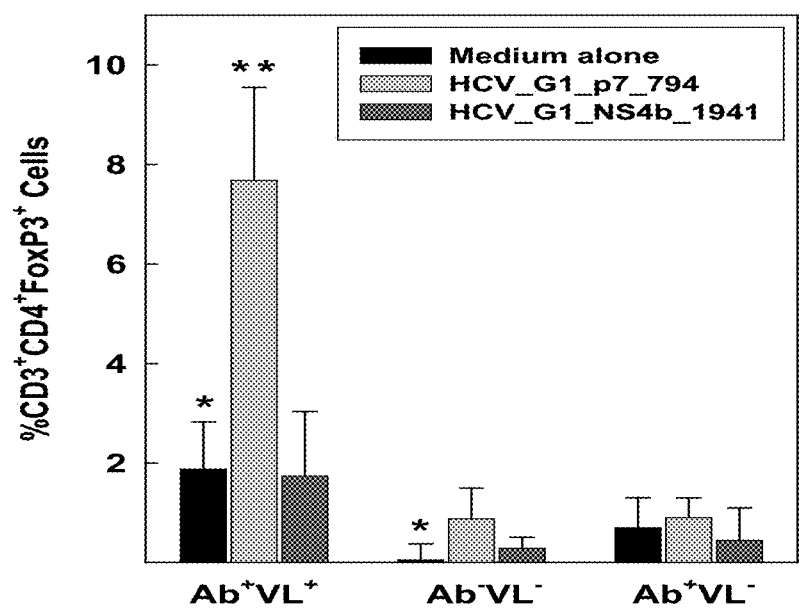

$Ab^+VL^+$ patients also had a higher baseline level of $CD3^+CD4^+Foxp3^+$ cells compared to spontaneously clearers and non-infected controls, a finding consistent with the literature (FIG. 2). PBMCs obtained from infected patients ($Ab^+VL^+$, n=4), patients who clear infection ($Ab^+VL^-$, n=6) and non-infected controls ($Ab^-VL^-$, n=4) were cultured in the presence of medium alone, 10 µg/ml HCV_G1_p7_794 or 10 µg/ml HCV_G1_NS4b_1941. The cells were collected after 5 days incubation, stained and analyzed by flow cytometry as outlined schematically in FIG. 1; *Significantly different, P=0.014; **significantly greater than all other groups, P<0.001.

Further, neither HCV_G1_p7_794 (putative Treg epitope) nor HCV_G1_NSB4_1941 (putative T effector epitope) added to PBMC cultures derived from non-infected individuals or from patients who successfully cleared HCV infection induced a significant increase in $CD3^+CD4^+FoxP3^+$ cells.

Example 3. HCV_G1_p7_794 Induces an Increase in $CD3^+CD4^+FoxP3^+$ T Cells in the Absence of Proliferation The hallmark of $CD3^+CD4^+FoxP3^+$ $T_{reg}$ cells is suppressor activity. CSFE-labeled, $Ab^+VL^+$ PBMCs were cultured with medium alone or medium that contained 30 ng/ml anti-CD3, 10 µg/ml HCV_G1_p7_794 or a combination of anti-CD3 and HCV_G1_p7_794. After 5 days incubation, the cells were collected and proliferation the total (FIG. 3BA) and $CD3^+CD4^+$ (FIG. 3B) PBMC populations was estimated by flow cytometry. Data were obtained in a single experiment representative of the results obtained for PBMCs derived from six HCV-infected patients.

$CD3^+CD4^+FoxP3^+$ T cells do not proliferate in response to HCV_G1_p7_794. PBMCs obtained from HCV-infected patients ($Ab^+VL^+$, n=4) and non-infected controls ($Ab^-VL^-$, n=4) were cultured in the presence or absence of 10 µg/ml of human p7_794 analog. The cells were collected after 5 days incubation and analyzed by flow. Significantly more $CD3^+CD4^+FoxP3^+$ cells were recovered from PBMC cultured with the human p7_794 analog than medium alone: *P=0.001; **P=0.048.

The addition of HCV_G1_p7_794 to $Ab^+VL^+$ PBMC cultures resulted in a reproducible, albeit slight, decrease in the proliferative response to anti-CD3 monoclonal antibody treatment whether the total (FIG. 3A) or $CD3^+CD4^+$ (FIG. 3B) cell population was assessed. Importantly, the addition of HCV_G1_p7_794 alone (i.e., in the absence of anti-CD3) had no effect on the proliferation of $CD3^+CD4^+$ T cells obtained from the same patient population. This finding suggests that HCV_G1_p7_794 induces the conversion of conventional $CD3^+CD4^+FoxP3^-$ T cells to $CD3^+CD4^+FoxP3^+$ $iT_{reg}$ cells, rather than stimulating the proliferation of $T_{reg}$ cells already present.

Example 4: HCV_G1_p7_794 Activates Cross-Reactive $nT_{reg}$ Cells and Induces Infectious Tolerance A human analog of HCV_G1_p7_794 (p7_794, PLLLLLLSLPPRA (SEQ ID NO: 2)) was identified by GenBank BLAST analysis and synthesized in an effort to provide a clearer understanding of the nature of the $T_{reg}$ cells that respond to HCV_G1_p7_794. Like the HCV-encoded homolog, the human analog induced a significant increase in $CD3^+CD4^+FoxP3^+$ cells in PBMC cultures derived from patients with persistent viremia (FIG. 4).

Human p7_794 analog stimulated a significant increase in $CD3^+CD4^+FoxP3^+$ T cells in HCV-infected and non-infected individuals. PBMCs obtained from HCV-infected patients ($Ab^+VL^+$, n=4) and non-infected controls ($Ab^-VL^-$, n=4) were cultured in the presence or absence of 10 µg/ml of human p7_794 analog. The cells were collected after 5 days incubation and analyzed by flow. Significantly more CD3+CD4+FoxP3+ cells were recovered from PBMC cultured with the human p7_794 analog than medium alone: *P=0.001; **P=0.048.

In contrast to HCV_G1_p7_794, the human analog also induced an approximate three-fold increase in CD3+CD4+ FoxP3+ cells in PBMC cultures derived from non-infected individuals indicating the response of an $nT_{reg}$ cell population.

CD304 (neuropilin-1) is expressed by a subset of FoxP3+ $T_{reg}$ cells in humans. In mice, CD304 expression differentiates natural (CD304+), from inducible (CD304−), $T_{reg}$ cells. PBMCs obtained from an infected patient (representative of 4 patients) were incubated in medium alone (A) or medium that contained 10 μg/ml HCV_G1_p7_794 (B). The cells were collected on day 5, stained and analyzed by flow. Panels on the right indicate the percentage of CD4+FoxP3+ cells in each population that expresses CD304. While a similar distinction has yet to be reported in humans, it is pertinent to note that the bulk of CD4+FoxP3+ cells contained among Ab+VL+ PBMCs cultured in the absence of HCV_G1_p7_794 expressed CD304 indicative of $nT_{reg}$ cells (FIG. 5A). In contrast, the vast majority of CD4+ FoxP3+ cells among Ab+VL+ PBMCs cultured in the presence of HCV_G1_p7_794 were CD304-negative characteristic of $iT_{reg}$ cells (FIG. 5B). Together these findings showed that HCV_G1_p7_794 recognition by $nT_{reg}$ cells following HCV exposure promotes infectious tolerance and the production of FoxP3+ $iT_{reg}$ cells from conventional CD4+ FoxP3− $T_{eff}$ cells.

Example 5: JanusMatrix Confirms $T_{reg}$ Cell Epitopes Shared by HCV_G1_p7_974 and the Human Proteome By comparing HCV G1_p7_794 with peptide sequences found within the human proteome, JanusMatrix analysis provided further insight into the capacity of HCV_G1_p7_794 to induce a $T_{reg}$ cell response by PBMCs derived from HCV-infected patients.

Crystal structure analyses of ternary, MHC:epitope: T cell receptor (TcR) complexes indicate that certain amino acid residues of a T cell epitope contact the MHC molecule while other residues contact the TcR. The TcR contacts can be modeled using a new bioinformatics tool, JanusMatrix. This tool interrogates potential T cell epitopes from both its HLA-binding and TcR-facing aspects, and assesses TcR cross-reactivity with T cell epitopes that are present in the human genome and in the human microbiome, or other genomes. Those epitopes from two different genomic sources, e.g., HCV and human, that bind the same HLA molecules and present identical amino acids to the TcR are designated potentially cross-reactive, as they may stimulate the same TcR and trigger the same T cell to respond. In the analysis, JanusMatrix divided the HCV HLA-DRB1-restricted epitopes (comprising the ICS described above) into TcR-facing and MHC-binding amino acid residues. The human protein database (UniProtKB) was searched for TcR-facing epitopes that cross-react with epitopes encoded by HCV.

As illustrated in Table 2, HCV_G1_p7_794 consists of 6 T cell epitopes, 5 of which cross-react with 152 putative human T cell epitopes contained in 264 different human proteins. Similarly, the human analog, p7_794, cross-reacts with putative T cell epitopes located within several hundred human proteins. On the other hand, neither HCV_G1_NS4b_1941 (control ICS often used in the ex vivo experiments described above) nor any of the other 18 ICS, which were originally predicted and validated (data not shown), exhibited significant cross-reactivity with the human proteome. The results of these analyses support the speculation that HCV_G1_p7_794 activates a cross-reactive $nT_{reg}$ cell population that normally functions to suppress autoimmune responses to a large number of human proteins, which contain a common peptide sequence (epitope).

TABLE 2

Comparison of Peptide Sequences

| Description | ICS Sequence | per ICS | # Cross-Reactive Epitopes in Human Proteins |
|---|---|---|---|
| HCV_G1_p7_794 | WPLLLLLLALPQ RAYAQ SEQ ID NO: 1 | 5.0 | 264 |
| Human p7_794 | PLLLLLLSLPPR A SEQ ID NO: 2 | 4.0 | 325 |
| HCV_G1_NS4b_1941 | AARVTQILSSLT ITQLLKRLHQWI SEQ ID NO: 3 | 6.0 | 28 |

The present invention demonstrated that ICS, HCV_G1_p7_794, induced a marked increase in $T_{reg}$ cells in PBMC cultures derived from infected patients, but not those patients who spontaneously cleared HCV or non-infected individuals. An analogous human peptide (p7_794), on the other hand, induced a significant increase in $T_{reg}$ cells among PBMCs derived from both HCV infected and non-infected individuals. JanusMatrix analyses determined that HCV_G1_p7_794 is comprised of $T_{reg}$ cell epitopes that exhibit extensive cross-reactivity with the human proteome.

This unique viral peptide derived from HCV p7 protein (HCV_G1_p7_794) promoted a $T_{reg}$ cell response among PBMCs derived from patients with persistent HCV infection. It also exhibited human homology when evaluated using GenBank Basic Local Alignment Search Tool (BLAST). Further analysis using a new bioinformatics tool, JanusMatrix, demonstrated that this HCV peptide cross-reacts with HLA matched peptide sequences located within hundreds of human proteins. The data demonstrated that HCV_G1_p7_794 engaged preexisting $nT_{reg}$ cells, as a consequence of this homology, induces infectious tolerance and the expansion an $iT_{reg}$ cell population, which contributes to suppression of effector $T_{(eff)}$ cell activity in cases of chronic HCV infection. It is concluded that HCV_G1_p7_794 with extensive human homology activates cross-reactive CD3+CD4+CD25+FoxP3+ $nT_{reg}$ cells, contributing potentially to immunosuppression and chronic hepatitis C.

The ability of HCV-derived epitopes to stimulate $T_{reg}$ cell responses is well documented; a number of HCV-encoded $T_{reg}$ cell epitopes derived from structural, as well as non-structural, HCV proteins have been reported. The invention described is the first to identify a promiscuous, HCV peptide sequence (HCV_G1_p7_794) that exhibits extensive human homology and the ability to induce $T_{reg}$ cells in vitro. HCV_G1_p7_794 added to PBMCs cultures derived from HCV-infected patients, but not from non-infected individuals or patients who cleared infection, induced a marked increase in CD3+CD4+FoxP3+ cells. In addition to expressing CD25, characteristic of $T_{reg}$ cells, the vast majority of these cells expressed CD39, a marker that distinguishes FoxP3+ T$_{reg}$ cells from activated T$_{eff}$ cells that transiently express FoxP3, but not suppressor activity.

In contrast to HCV_G1_p7_794, the human peptide analog (p7_794) elicited a significant increase in CD3+CD4+ FoxP3+ cells in PBMC cultures derived from non-infected individuals with no evidence of prior HCV exposure, as well as HCV-infected patients. This finding is congruent with the suggestion that viral epitopes with human homology influence the pathogenesis of chronic HCV by activating preexisting, cross-reactive nT$_{reg}$ cells. Indeed, extensive homology between the HCV polyprotein and proteins that comprise human proteome is well documented. JanusMatrix, a bioinformatics algorithm that interrogates potential T cell epitopes from both their HLA-binding and TcR-facing aspects, confirmed the existence of significant homology between HCV_G1_p7_794 and hundreds of proteins that compose the human proteome. The results of this analysis demonstrate the potential efficacy of JanusMatrix in identifying pathogen-encoded epitopes that elicit the activity of nT$_{reg}$ cells, which normally function to suppress autoimmune reactivity to self antigens (proteins). In this regard, it is pertinent to remark that HCV_G1_p7_794 is comprised of epitopes that are homologous to those found in hundreds of human proteins. This suggests the autoimmune response to a large number of proteins is inhibited by a single or limited number of nT$_{reg}$ cell clones responsive to a common peptide sequence, rather than a large number of clones each responsive to a unique sequence in each protein.

Although immunosuppression is a defining characteristic of T$_{reg}$ cells and readily demonstrated in animal (mouse) models, demonstrating the suppressor activity of human CD3+CD4+CD25+FoxP3+ T$_{reg}$ cells in vitro, however, has proven problematic. Thus, while HCV_G1_p7_794 induced a 3- to 4-fold increase in CD3+CD4+CD25+FoxP3+ cells in PBMC cultures derived from HCV-infected patients in the studies reported here, these cells exerted only a limited effect on the nonspecific proliferative response of cells stimulated with anti-CD3. Recent studies indicate that the nature of the responder T cells (CD4+CD25− versus CD4+CD25$^{low}$) and the ratio of purified T$_{reg}$ cells to purified responder cells exert significant effects on the outcome of suppression assays. Notably, in the experiments reported here, HCV_G1_p7_794 was added to heterogeneous PBMC cultures in which the CD3+CD4+FoxP3− responder, far outnumbered the CD3+CD4+CD25+FoxP3+ suppressor, cells by >10:1. Importantly, the addition of HCV_G1_p7_794 alone to PBMC cultures derived from HCV-infected (Ab+ VL+) patients failed to induce cell proliferation despite a marked (3- to 4-fold) increase in CD3+CD4+CD25+FoxP3+ cell number. This finding suggests that HCV_G1_p7_794 induces the conversion of conventional T$_{eff}$ to T$_{reg}$ cells, i.e., infectious tolerance, a suggestion supported by studies demonstrating the inability of nT$_{reg}$ cells to proliferate in response to their cognate antigen in vitro. Furthermore, in contrast to Ab+VL+ PBMCs cultured in medium alone, only a minority of CD3+CD4+FoxP3+ cells derived from PBMCs cultured in the presence of HCV_G1_p7_794 expressed CD304 (neuropilin), which is expressed by a subset of FoxP3+ T$_{reg}$ cells in humans and associated specifically with nT$_{reg}$ cells in mice. While it has been suggested alternatively that the expanded T$_{reg}$ cell population in chronic, HCV infected patients is composed of cells phenotypically similar to nT$_{reg}$ or iT$_{reg}$ cells, our results concur with the consensus that the expanded T$_{reg}$ cell population in chronic HCV-infected patients is heterogeneous, composed of both T$_{reg}$ cell subsets.

Taken together, the findings showed that HCV non-structural protein p7 contains a unique peptide sequence (HCV_G1_p7_794), which is recognized by the TcR repertoire expressed by nT$_{reg}$ cells that function normally to suppress the autoimmune response to hundreds of human proteins. Upon HCV_G1_p7_794 recognition, these nT$_{reg}$ cells induce the conversion of conventional T$_{eff}$ cells to iT$_{reg}$ cells (i.e. infectious tolerance). It is expected that the nT$_{reg}$ cells and iT$_{reg}$ cells responsive to HCV_G1_p7_794 contribute to the elevated T$_{reg}$ cell population found in HCV-infected patients, and play a role in immunosuppression and viral persistence.

Those skilled in the art will appreciate that numerous modifications and variations may be made to the above disclosed embodiments and contained in the claims without departing from the spirit and scope of the present invention.

What is claimed is:

1. A pharmaceutical composition comprising an isolated T-cell epitope peptide adapted to repress an immune response and a pharmaceutically acceptable carrier or excipient; said peptide consists of an amino acid sequence of PLLLLLLXLPXRA (SEQ ID NO:5), wherein X is an amino acid and does not have to be the same amino acid in each occurrence in a given sequence.

2. The pharmaceutical composition of claim 1, wherein the PLLLLLLXLPXRA peptide is selected from the group consisting of PLLLLLLSLPPRA (SEQ ID NO:2) and PLLLLLLALPQRA (SEQ ID NO:6).

3. The pharmaceutical composition of claim 1, further comprising a target antigen.

4. An isolated T-cell epitope peptide, consisting of an amino acid sequence of PLLLLLLXLPXRA (SEQ ID NO:5), wherein X is an amino acid and does not have to be the same amino acid in each occurrence in a given sequence.

5. The T-cell epitope peptide of claim 4, wherein the PLLLLLLXLPXRA sequence is selected from the group consisting of PLLLLLLSLPPRA (SEQ ID NO:2) and PLLLLLLALPQRA (SEQ ID NO:6).

6. A nucleic acid encoding the T-cell epitope peptide of claim 5.

7. A vector comprising the nucleic acid of claim 6.

8. An isolated cell comprising the vector of claim 7.

9. A pharmaceutical composition comprising an isolated T-cell epitope peptide adapted to repress an immune response and a pharmaceutically acceptable carrier or excipient; wherein said peptide is 13-25 amino acids long and comprises a sequence of PLLLLLLXLPXRA (SEQ ID NO:5), wherein X is an amino acid and does not have to be the same amino acid in each occurrence in a given sequence, provided that said peptide does not contain PLLLLLLA-LPQRA (SEQ ID NO:6).

10. The pharmaceutical composition of claim 9, wherein the PLLLLLLXLPXRA sequence is PLLLLLLSLPPRA (SEQ ID NO:2).

11. The pharmaceutical composition of claim 9, further comprising a target antigen.

12. The pharmaceutical composition of claim 10, further comprising a target antigen.

13. The pharmaceutical composition of claim 2, further comprising a target antigen.

\* \* \* \* \*